United States Patent
Hossain et al.

[11] Patent Number: 6,063,021
[45] Date of Patent: May 16, 2000

[54] STABILIZER FOR SURGERY

[75] Inventors: Mosaddeq Hossain, Somerville, N.J.; Victor Markus, Lower Gwynedd; John A. Fanticola, N. Wales, both of Pa.; Robert Banik, Long Valley, N.J.; Gerard A. Powell, Havertown, Pa.

[73] Assignee: Pilling Weck Incorporated, Fort Washington, Pa.

[21] Appl. No.: 09/127,419

[22] Filed: Jul. 31, 1998

[51] Int. Cl.[7] .................................................. A61F 2/00
[52] U.S. Cl. ................................................................ 600/37
[58] Field of Search ........................... 600/37, 210, 235; 128/897–898; 606/1, 191, 205–208

[56] References Cited

U.S. PATENT DOCUMENTS

| | | | |
|---|---|---|---|
| 1,396,427 | 11/1921 | Hatch | 606/1 |
| 5,727,569 | 3/1998 | Benetti et al. | |
| 5,738,675 | 4/1998 | Botimer | 606/1 |
| 5,782,746 | 7/1998 | Wright | 600/37 |
| 5,836,311 | 11/1998 | Borst et al. | |
| 5,894,843 | 4/1999 | Benetti et al. | |

*Primary Examiner*—Samuel G. Gilbert
*Attorney, Agent, or Firm*—Howson & Howson

[57] ABSTRACT

A stabilizer is used to immobilize a portion of the heart or other organ to facilitate a surgical procedure such as anastomosis. The stabilizer comprises two, C-shaped, organ wall-contacting elements, hinged together so that they can form a continuous loop. The hinge allows the C-shaped elements to be separated so that, after surgery in which a tubular graft connected to the organ extends through the loop, the stabilizer can be released from the graft. The C-shaped elements are connected to a stem which consists of two lockably articulating parts, one of which is immediately connected to one of the C-shaped elements and aligned with the hinge axis. A spring-loaded sleeve, surrounding the last-mentioned part of the stem, has pins which engage recesses in the C-shaped parts to lock them in the closed condition, while allowing them to be opened quickly by manipulation of the sleeve. Removable, disposable pads form the organ wall-contacting surfaces. An optional light carrier provides illumination, and ports are provided in one of the C-shaped elements for suction and/or irrigation.

16 Claims, 8 Drawing Sheets

STABILIZER FOR SURGERY

SUMMARY OF THE INVENTION

This invention relates to surgery and particularly to a surgical instrument for reducing the movement of a body organ during surgery, so that a surgeon can carry out a procedure on that organ. Although not limited to use in heart surgery, the invention has particular utility as a heart stabilizer for enabling a procedure such as a coronary artery bypass to be carried out without stopping the heart.

As used herein, the terms "stabilize" and "immobilize" should be understood as referring to reduction of the natural movement of a portion of an organ, by mechanical means, sufficiently to facilitate suturing and other surgical procedures on that organ.

As explained in U.S. Pat. No. 5,727,569, granted Mar. 17, 1998, the ability to fix the position of cardiac tissue in a particular region of the heart permits the surgeon to carry out delicate surgical procedures on the beating heart while the portion of the heart on which the surgery is performed remains substantially motionless throughout the procedure. The instruments described in U.S. Pat. No. 5,727,569 utilize a plurality of suction ports in a surface of the instrument to immobilize a portion of the heart while reducing trauma to the tissue caused by the negative pressure. The use of suction ports is described as an improvement over a prior method in which the surgeon passes sutures through exterior tissue layers of the heart and pulls the sutures in opposite directions, stretching the tissue and thereby reducing or partially compensating for the motion caused by contractions of the heart muscles.

In several of the embodiments of the instrument described in U.S. Pat. No. 5,727,569, the heart-contacting device is circular or oval in shape. In carrying out a coronary artery bypass graft by anastomosis, the blood vessel which is being connected to the coronary artery must be located between the heart-contacting surface of the instrument and the outer wall of the heart. Otherwise, the instrument could not be removed. The vessel which is being connected to the coronary artery must therefore be carefully placed in the proper position before the instrument is brought into contact with the heart wall. To prevent damage to the graft, the heart wall-contacting surface of the instrument is preferably discontinuous, having one or more gaps to accommodate the graft.

With other embodiments, in which the heart-contacting surface of the instrument is semi-oval or U-shaped, or consists of two separate, parallel sections, the instrument can be brought into contact with the heart before the graft is set in place, and it can be removed after anastomosis. However, the instruments having semi-oval, U-shaped or plural separate surfaces are not as effective as the circular and oval instruments in holding a portion of the heart immobilized.

The principal object of this invention is to provide a stabilizing instrument which contacts the wall of the heart or other moving organ over an area in the form of a substantially continuous, closed loop, but which can be removed readily after anastomosis of a graft.

Another object of the invention is to provide for easy adjustment of the position of the organ wall-contacting surface of the instrument.

Still other objects of the invention include the avoidance of damage to the organ, the provision of readily replaceable compressible pads which form the organ wall-contacting surfaces, the provision of ports for drawing off fluids by suction and for irrigation, and improved illumination of the surgical site.

The stabilizer in accordance with this invention comprises a pair of organ wall-contacting elements each having a first end, a second end and a organ wall-contacting surface. The elements are hinged together by a hinge connecting the first ends of the organ wall-contacting elements so that one of the organ wall-contacting elements can rotate relative to the other about a hinge axis. The hinge axis extends transverse to the organ wall-contacting surfaces. The second ends can meet each other and separate from each other by rotation of one of said organ wall-contacting elements relative to the other about the hinge. The organ wall-contacting elements are shaped to form a loop having a central opening when the second ends meet, so that the organ wall-contacting surfaces can contact the wall of the organ over an area substantially in the form of a continuous closed loop.

In a preferred embodiment, a spring urges the second ends of the organ wall-contacting elements apart from each other. The organ wall-contacting elements have overlapping parts with holes which become aligned with each other in a direction parallel to the hinge axis when the second ends of the organ wall-contacting elements meet each other. A locking pin extends through the holes, when they are aligned, to lock the organ wall-contacting elements in fixed relationship to each other. The locking pin is preferably a projection on a movable collar surrounding a section of a stem of the stabilizer which extends along the hinge axis. The projection is releasable from at least one of the holes by manual movement of the collar along the hinge axis. Thus, by moving the collar in a first direction along the hinge axis, the heart wall-contacting elements can be unlocked, so that the second ends thereof can separate from each other. Preferably, a spring is provided to urge the collar in the opposite direction so that the organ wall-contacting elements are automatically locked in the closed condition when their second ends come together.

The stem preferably comprises a first stem section fixed to one of the organ wall-contacting elements, and a second stem section connected to the first stem section by a releasably lockable, articulating joint. The second stem section is hollow and has a rod extending lengthwise within it. The joint comprises a ball fixed to the first stem section and a socket connected to one end of the second stem section. By manual rotation of a sleeve at the opposite end of the second stem section, the rod is urged against the ball to lock the articulating joint, so that the first stem section is held in fixed relationship to the second stem section.

In a preferred embodiment of the stabilizer, each organ wall-contacting element includes a compressible pad, and the organ wall-contacting surface of each such element is a surface of the pad thereof. Each organ wall-contacting element comprises a rigid part and a pad assembly removably affixed thereto, the pad assembly comprising a flexible pad and a pad-supporting member. The pad-supporting member of the pad assembly of each organ wall-contacting element has plural projections mating with holes in the rigid part. The projections fit into their mating holes with a snap fit.

Either or both of the organ wall-contacting members may also include a plurality of ports connected to a conduit for suction to remove fluids, or for irrigation of the surgical site.

Either or both of the organ wall-contacting members may also have an attached light-emitting member connected to receive light through a flexible, light-transmitting conduit.

Other objects, details and advantages of the invention will be apparent from the following detailed description when read in conjunction with the drawings.

DETAILED DESCRIPTION

The invention will now be described with reference to a specific embodiment designed for use as a heart stabilizer.

Figure 1:
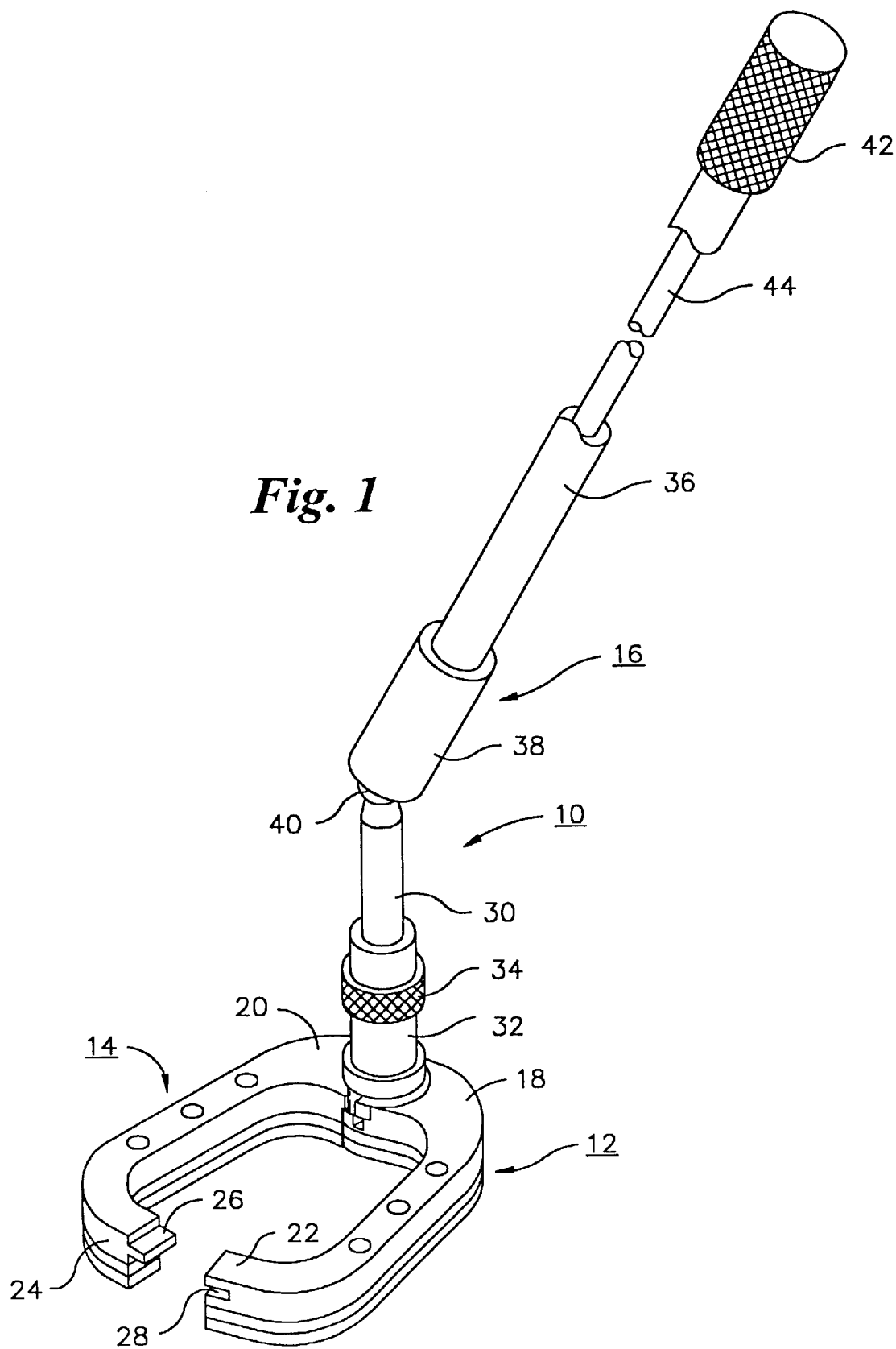
FIG. 1 is a perspective view showing a heart stabilizer, in accordance with a first embodiment of the invention, with its hinged, heart wall-contacting elements of the foot in an opened condition.

As shown in FIG. 1, the heart stabilizer 10, in accordance with a first embodiment of the invention, comprises a pair of opposed, C-shaped heart wall-contacting elements 12 and 14 at the lower end of an articulated stem 16.

Figure 2:
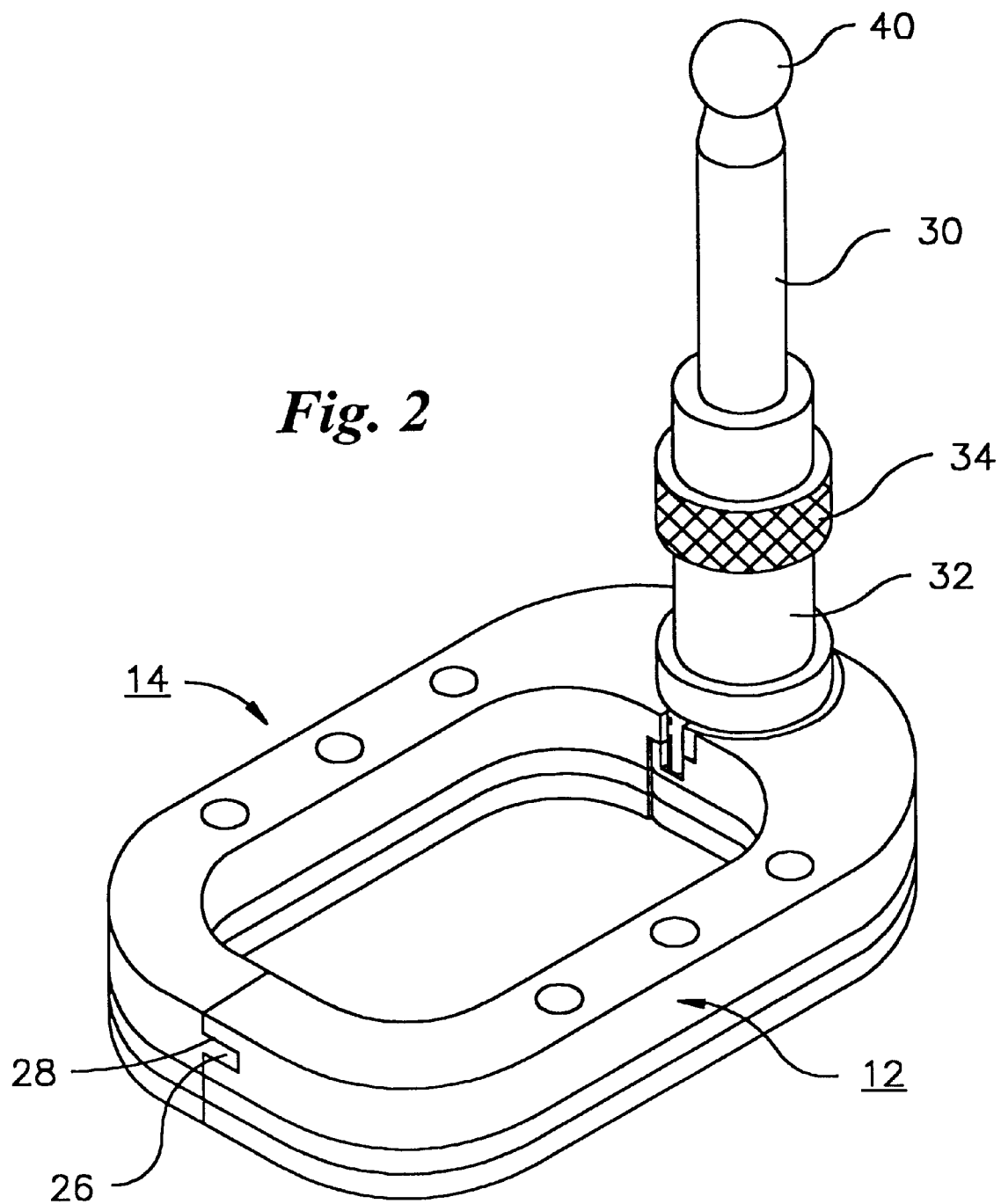
FIG. 2 is a fragmentary perspective view showing the heart stabilizer with its heart wall-contacting elements in a closed condition.
Figure 3:
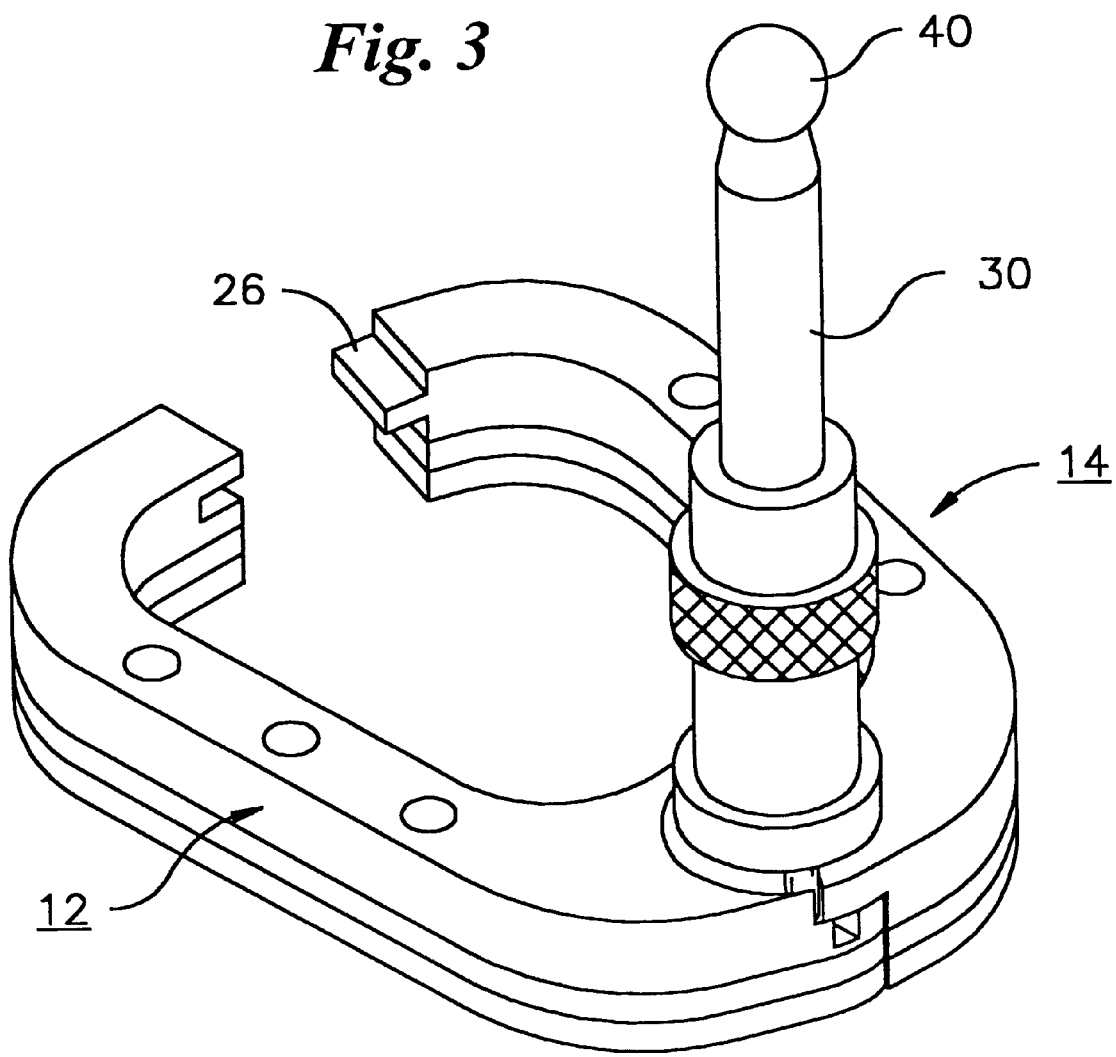
FIG. 3 is a fragmentary perspective view showing the rear of the heart stabilizer.

The elements 12 and 14 have first ends 18 and 20 respectively, which are hinged together, and second ends 22 and 24, which are shown separated from each other in FIG. 1. The second ends 22 and 24 can be brought together as shown in FIG. 2, with a tongue 26 on element 14 mating with a groove 28 in element 12.

Figure 7:
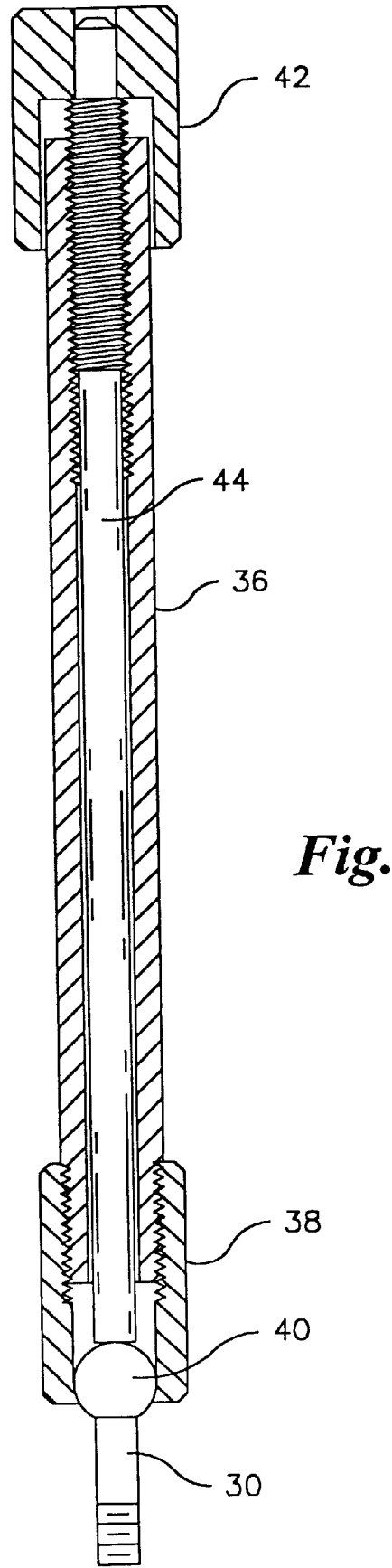
FIG. 7 is a vertical section through the supporting rod of the stabilizer, showing the manner of adjusting the angular position of the foot relative to the rod.

The stem 16 comprises a short stem section 30, which is fixed to element 12 and aligned with the axis of the hinge which connects elements 12 and 14. The lower part of stem section 30 is surrounded by a sleeve 32, having a knurled grasping part 34. As will be explained later in greater detail, the sleeve is urged downward by an internal spring, and has projections capable of locking the elements 12 and 14 in the position shown in FIG. 2, that is, with their ends 22 and 24 together to form a closed loop. The upper part of the stem includes a longer, hollow section 36. As shown in FIG. 7, this longer section has a socket 38 at its lower end, mating with ball 40 formed at the upper end of stem section 30. A knurled cap 42 is fixed to the upper end of an internal rod 44, which extends through section 36. The upper part of rod 44 has threads which are engaged with internal threads in the upper part of hollow section 36. By rotating the knurled element, the internal rod 44, extending lengthwise within the hollow stem section 36, can be pressed against ball 40. This pulls the socket 38 upward against the underside of the ball, as the rod bears downward against the upper part of the ball, thereby tightening the ball and socket joint and securing the stem sections 30 and 36 against articulation.

Figure 4:
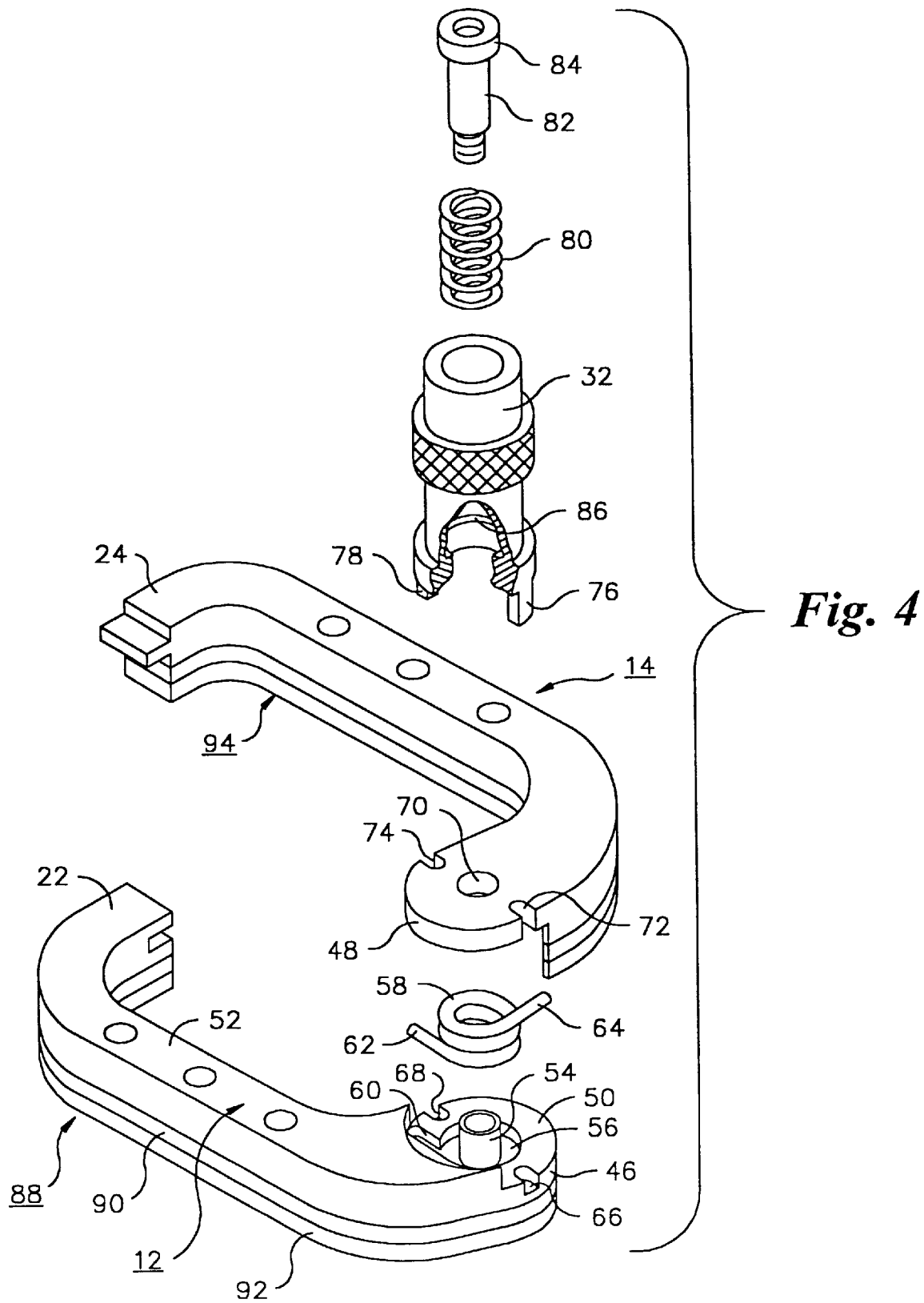
FIG. 4 is an exploded view of the heart stabilizer of FIGS. 1, 2 and 3.

As shown in exploded view in FIG. 4, elements 12 and 14 have overlapping parts 46 and 48 respectively, which form the hinge. Part 46, on element 12, has an annular upper face 50, which is recessed below the upper face 52 of the forward extending part of element 12. Part 46 has a centrally located, hollow, upright, circular, cylindrical projection 54, with internal threads for connection to the threaded lower end of stem section 30. Surrounding this projection 54, and located between projection 54 and annular upper face 50, is an annular recess 56 for receiving the coiled part of a metal spring 58. A radial slot 60, connected to recess 56 and extending into annular face 50, is provided to receive a straight end part 62 of spring 58.

Part 48, on element 14 has an annular recess and a straight, radial slot (not shown), similar to recess 56 and radial slot 60, for accommodating the upper part of coil 58 and straight part 64 of the spring. The spring, and the radial slots in parts 46 and 48 are configured so that the spring urges elements 12 and 14 toward their opened condition, i.e. the condition in which their second ends 22 and 24 are separated from each other.

Part 46 also has recesses 66 and 68, opposite each other, on the outer parts of its annular upper face 50. Part 48 has a through hole 70, which receives projection 54. The size of projection 54 is such that it fits into hole 70 with almost no play. Therefore, when projection 54 is located within hole 70, the elements 12 and 14 can rotate relative to each other about the axis of projection 54, without translation or tilting relative to the axis.

The outer edge of part 48 has slots 72 and 74, opposed to each other on opposite sides of hole 70. These slots are positioned to be aligned respectively with recesses 66 and 68 when ends 22 and 24 are together. Pins 76 and 78, which extend downward from sleeve 32, extend, through slots 72 and 74 respectively, into recesses 66 and 68 to lock the elements 12 and 14 in the closed condition. The elements can be released by manually pushing upward on sleeve 32 to disengage pins 76 and 78 from recesses 66 and 68.

Sleeve 32 is continuously urged downward (in the locking direction) by an internal coil spring 80, to ensure against accidental release of the elements 12 and 14 from their locked condition, and to lock the elements in their closed condition automatically as their ends 22 and 24 are brought together. Spring 80 surrounds a pin 82, the lower end of which is threaded into projection 54. The spring is in compression between a collar 84 formed on pin 82 and an annulus 86 formed inside sleeve 32 near its lower end.

Still referring to FIG. 4, the upper part of element 12, which includes hinge part 46, is preferably formed from stainless steel or other metal or plastics material suitable for a surgical instrument. Underneath the upper part is a pad assembly 88, which comprises a rigid pad-supporting member 90 and a compressible pad 92. The pad-supporting member is preferably molded from a suitable plastics material, and the pad itself, which is adhesively secured to the supporting member, is formed from a closed-cell foamed plastics material.

Element 24 has a similar pad assembly 94. The pad assembly of each heart wall-engaging element 12 and 14 preferably extends from a location adjacent the hinge axis to the opposite end of the element, so that the pads closely approach each other at both ends, forming nearly a complete ring when the two elements 12 and 14 are in their closed condition. The hinge ends of the pad assemblies 88 and 92 can be concave and convex arcs concentric with the hinge axis and conforming to each other in order to avoid any significant gap between them.

Figure 5:
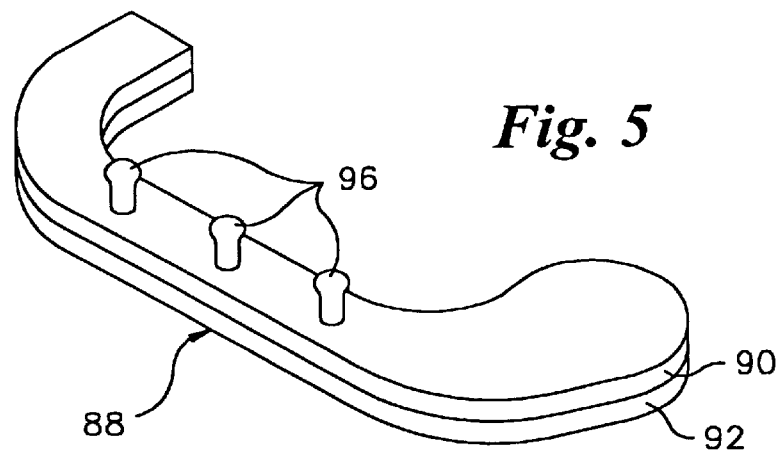
FIG. 5 is a perspective view of a pad which constitutes a part of one of the hinged organ wall-contacting elements in a preferred embodiment of the invention.
Figure 6:
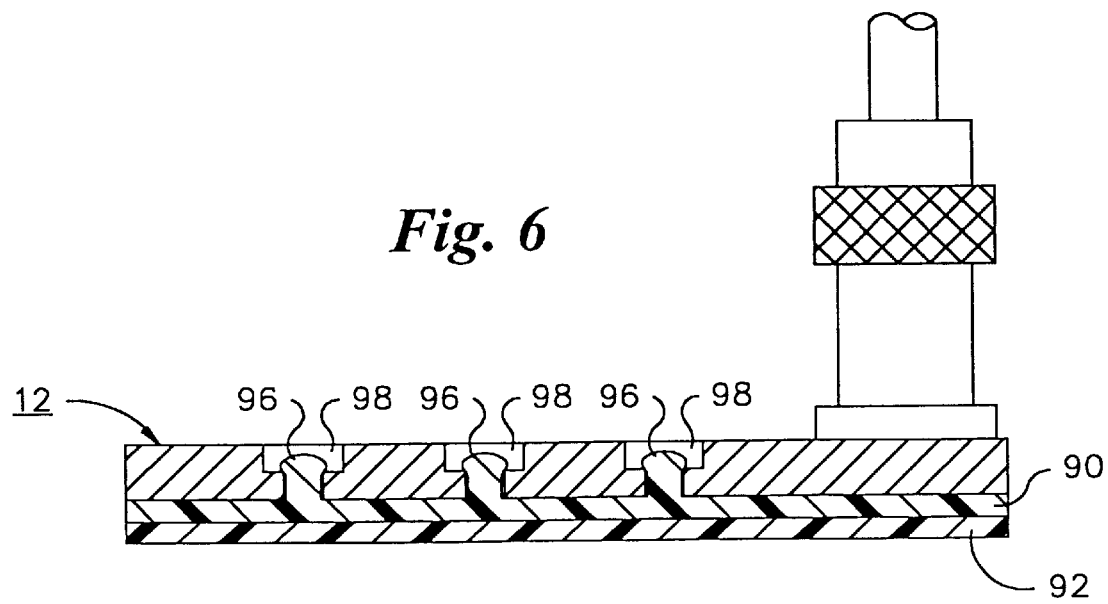
FIG. 6 is a vertical section through one of the heart wall-contacting elements, showing the manner in which the pad is attached to a metal component of the element.

As shown in FIG. 5, the rigid part 90 of pad assembly 88 has three upward projections 96, which fit into mating holes in the upper part of the element 12. At the upper end of each projection is a compressible enlargement which, when relaxed, is slightly larger than its mating hole, so that the projections fit into their mating holes with a snap fit. Thus, as seen in FIG. 6, projections 96 extend through holes in the upper part of element 12, with their enlargements disposed in recesses 98.

The pad assemblies are disposable, and can be prepackaged in sterilized condition and quickly attached to the remainder of the instrument, which is autoclaved before each use.

As shown in FIG. 7, the cap 42 is fixed to the upper end of rod 44. The upper end of the rod has threads which are engaged with threads in the upper end of the hollow, tubular stem section 36. Consequently, the rod can be moved axially by manual rotation of cap 42. The sleeve 38, which is engaged with the underside of ball 40 is threaded onto the lower end of stem section 36. Clockwise rotation of the cap 42 pushes the rod 44 downward against the upper part of the ball, and at the same time pulls sleeve 38 upward against the lower part of the ball. Consequently, the upper stem section can be locked frictionally to the lower stem section to prevent articulation. The upper stem section can be clamped to a retractor support (not shown) which can be mounted, for example, on a side rail of an operating table, or on a sternal retractor having a suitable provision for mounting of auxiliary retractors.

In operation, the stabilizer, with its elements 12 and 14 closed, is positioned against the heart wall over a coronary artery requiring by-pass, with the location to which the graft is to be attached exposed through the opening formed by the C-shaped, heart wall-contacting elements 12 and 14. The heart wall-contacting elements are pressed against the heart to immobilize the area to which the graft is to be attached, and secured in a fixed condition by tightening the clamp (not shown) by which the upper stem section 36 is connected to a retractor support, and tightening cap 42 to prevent articulation of the stem sections of the instrument. The graft is then connected to the artery by anastomosis. At this time, the other end of the graft will already have been attached to the aorta, and consequently it extends, through the opening between elements 12 and 14, from the aorta to the coronary artery, rather than underneath one of elements 12 and 14. To remove the instrument, the surgeon can simply pull upward on sleeve 32 to unlock elements 12 and 14. These elements then separate from each other automatically by the operation of spring 58 (FIG. 4), and the instrument can be quickly disengaged from the heart.

Figure 8:
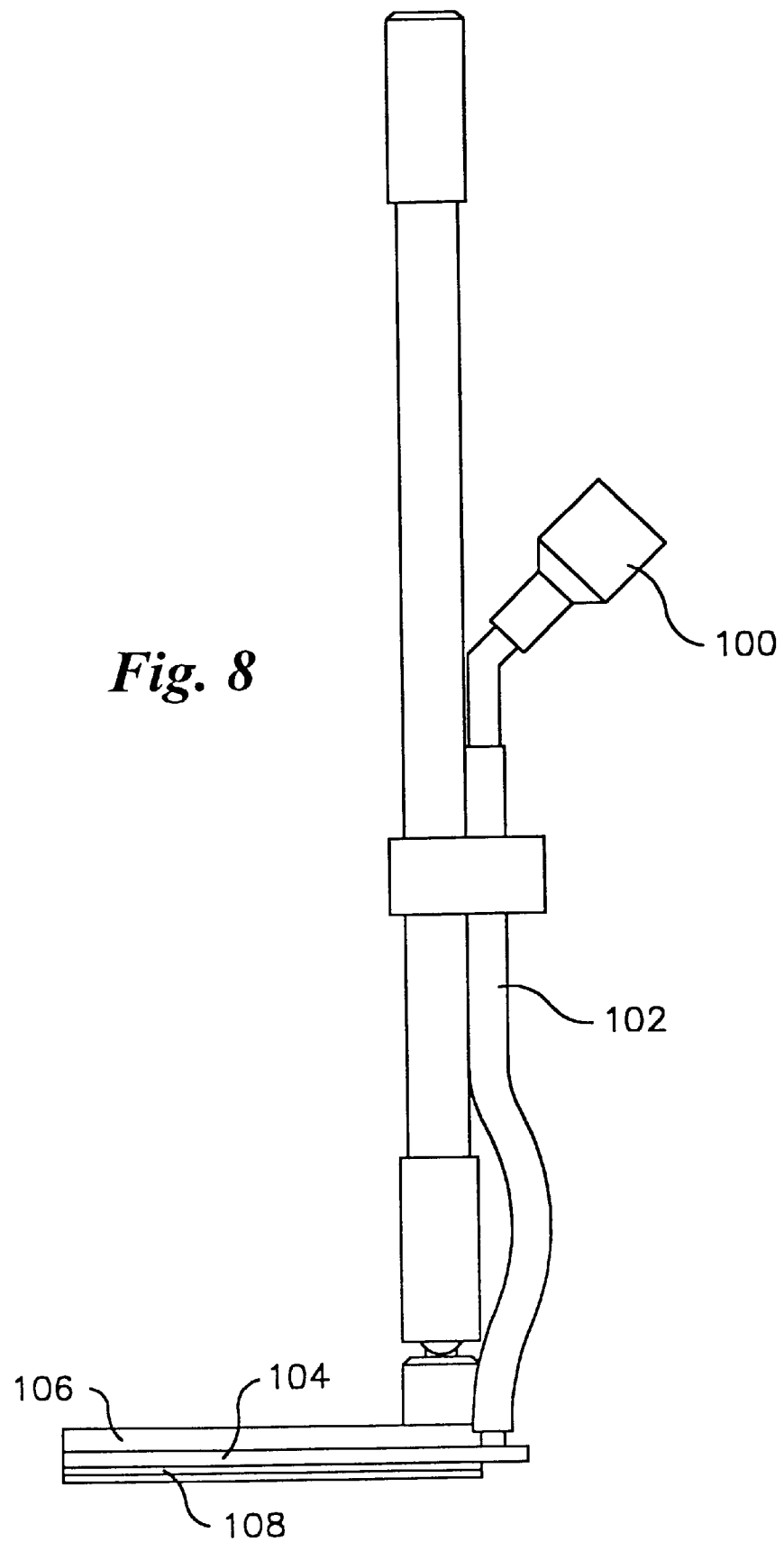
FIG. 8 is an elevational view of a modified version of the stabilizer, having a light-conducting illumination layer.

An auxiliary element, such as an illuminator for illumination of the surgical site, can be incorporated into the instrument, as shown in FIG. 8. A light source is connected through a fiber-optic light-conducting cable to connector 100. Light is conducted through a flexible fiber-optic cable 102 to an acrylic light-transmitting element 104 which is built into one of the heart wall-contacting elements between the hinged part 106 and the pad support 108. Element 104 conducts light to the surgical site within the opening between the heart wall-contacting elements. The auxiliary light transmitted through element 104 avoids shadows and facilitates the delicate surgical operations taking place, the view of which might otherwise be inadequate under the light provided by conventional overhead OR lighting and surgeon's headlamps. Although only one of the two heart wall-contacting elements in FIG. 8 is provided with a light-emitter, it should be understood that light-emitters can be provided on both elements. In the case of a single light-emitter on one of the two heart wall-contacting elements, the opposite element should be made sufficiently thick so that the heart wall-contacting surfaces of both elements are substantially continuous.

Figure 9:
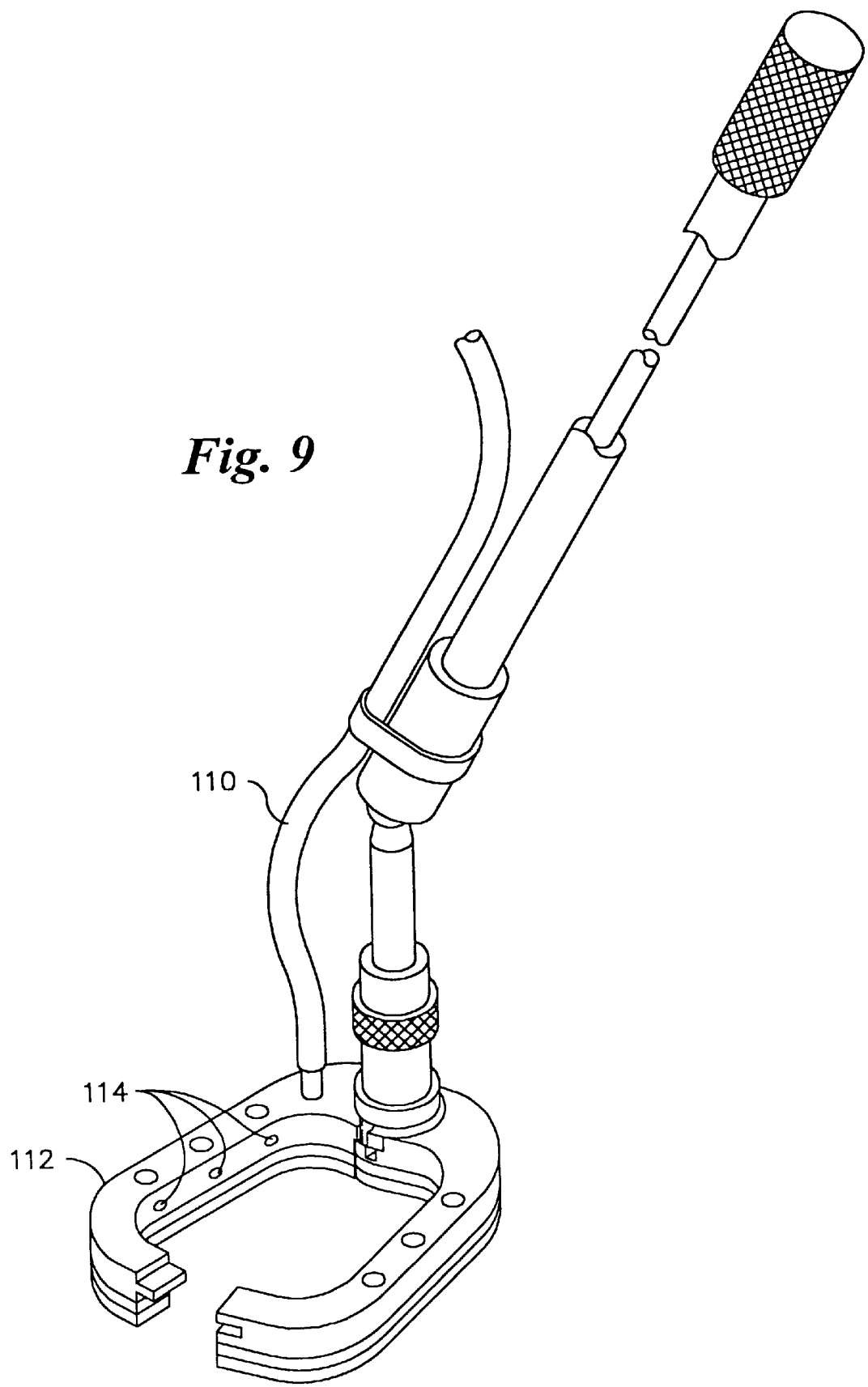
FIG. 9 is a perspective view of a modified version of the stabilizer, having passages and an attachment for suction.

One or both of the heart wall-contacting elements can be provided with ducts for suction to draw excess fluids away from the surgical site, or to introduce irrigation. As shown in FIG. 9, a flexible tube 110 is connected to element 112, which has an internal passage (not shown) providing communication between tube 110 and inwardly facing openings 114. Suction and irrigation openings can be provided in both of the heart wall-contacting elements, if desired.

It should be understood that the instrument, although described with particular reference to heart surgery, can be used to immobilize parts of other organs, such as the stomach, the intestines, the lungs, the aorta, etc. For example, the stabilizer can be used for anastomosis in procedures such as gastrostomy, colostomy, etc.

Various modifications can be made to the instruments described. For example, although the alignment of the hinge axis with the axis of the lower stem element is desirable for simplicity and ease of operation, it is possible to achieve some of the objectives of this invention with a stabilizer foot having a gate hinged at a location spaced from the stem. It is also possible to provide a stabilizer with a non-articulating, relatively stiff, but bendable, stem formed of a plastic material, i.e. metal or plastics which can be deformed permanently under load.

Still other modifications may be made to the apparatus and method described above without departing from the scope of the invention as defined in the following claims.

We claim:

1. A stabilizer for immobilizing a portion of the wall of an organ during surgery comprising:
    a pair of organ wall-contacting elements each having a first end, a second end and an organ wall-contacting surface; and
    a hinge connecting the first ends of the organ wall-contacting elements wherein one of said organ wall-contacting elements can rotate relative to the other about a hinge axis transverse to the organ wall-contacting surfaces;
    the second ends of the organ wall-contacting elements being positioned relative to their first ends so that they can meet each other and separate from each other by rotation of said one of said organ wall-contacting elements relative to the other about the hinge, and the organ wall-contacting elements being shaped to form a loop having a central opening when said second ends meet, wherein the organ wall-contacting surfaces can contact the wall of an organ over an area substantially in the form of a continuous closed loop.

2. A stabilizer according to claim 1, including spring means for urging the second ends of the organ wall-contacting elements apart from each other.

3. A stabilizer according to claim 1, including spring means for urging the second ends of the organ wall-contacting elements apart from each other, in which said organ wall-contacting elements have overlapping parts, and holes in said overlapping parts which are aligned with each other in a direction parallel to the hinge axis when the second ends of the organ wall-contacting elements meet each other, and a locking pin extendible through said holes, when the holes are aligned with each other, for locking the organ wall-contacting elements in fixed relationship to each other.

4. A stabilizer according to claim 1, in which said organ wall-contacting elements have overlapping parts, and holes in said overlapping parts which are aligned with each other in a direction parallel to the hinge axis when the second ends of the organ wall-contacting elements meet each other, and a locking pin extendible through a hole of one of said overlapping parts and into a hole of the other of said overlapping parts, when the holes are aligned with each other, for locking the organ wall-contacting elements in fixed relationship to each other.

5. A stabilizer according to claim 1, including a stem having a stem section extending along the hinge axis, and a sleeve surrounding said stem section and movable along said stem section in the direction of the hinge axis, and in which said organ wall-contacting elements have overlapping parts, and holes in said overlapping parts which are aligned with each other in a direction parallel to the hinge axis when the second ends of the organ wall-contacting elements meet each other, the sleeve having a projection extendible through a hole of one of said overlapping parts into a hole of the other of said overlapping parts, when the holes are aligned with each other, for releasably locking the organ wall-contacting elements in fixed relationship to each other, and releasable from at least one of said holes by movement of the sleeve along the hinge axis to unlock the organ wall-contacting elements so that the second ends thereof can separate from each other.

6. A stabilizer according to claim 1, including a stem having a stem section extending along the hinge axis, and a sleeve surrounding said stem section and movable along said stem section in the direction of the hinge axis, and in which said organ wall-contacting elements have overlapping parts, and holes in said overlapping parts which are aligned with each other in a direction parallel to the hinge axis when the second ends of the organ wall-contacting elements meet each other, the sleeve having a projection extendible through a hole of one of said overlapping parts into a hole of the other of said overlapping parts, when the holes are aligned with each other, for releasably locking the organ wall-contacting elements in fixed relationship to each other, and releasable from at least one of said holes by movement of the sleeve in a first direction along the hinge axis to unlock the organ wall-contacting elements so that the second ends thereof can separate from each other, and further including spring means urging said sleeve in a direction along the hinge axis opposite to said first direction.

7. A stabilizer according to claim 1, including a stem having a first stem section fixed to one of said organ wall-contacting elements, and a second stem section connected to said first stem section by a releasably lockable, articulating joint.

8. A stabilizer according to claim 1, including a stem having a first stem section fixed to one of said organ wall-contacting elements, and a second, hollow, elongated stem section having first and second ends, the first end being connected to said first stem section by an articulating joint comprising a ball fixed to the first stem section and a socket connected to the second stem section, and including a rod extending lengthwise within the second stem section, and manipulable means, at the second end of the second stem section for urging said rod against the ball to lock the articulating joint whereby the first stem section can be held in fixed relationship to the second stem section.

9. A stabilizer according to claim 1, including a stem having first and second articulable sections, the first section of the stem being fixed to one of said organ wall-contacting elements and aligned with said hinge axis.

10. A stabilizer according to claim 1, in which each organ wall-contacting element comprises a compressible pad, and in which the organ wall-contacting surface of each said element is a surface of the pad thereof.

11. A stabilizer according to claim 1, in which each organ wall-contacting element comprises a rigid part having a compressible pad affixed thereto, and in which the organ wall-contacting surface of each said element is a surface of the compressible pad thereof.

12. A stabilizer according to claim 1, in which each organ wall-contacting element comprises a rigid part having a compressible pad removably affixed thereto, and in which the organ wall-contacting surface of each said element is a surface of the compressible pad thereof.

13. A stabilizer according to claim 1, in which each organ wall-contacting element comprises a rigid part having a plurality of holes and a pad assembly removably affixed thereto, the pad assembly comprising a flexible pad and a rigid pad-supporting member, the rigid pad-supporting member of the pad assembly of each organ wall-contacting element having plural projections mating with the plurality of holes in the rigid part of said organ wall-contacting element, in which the organ wall-contacting surface of each said element is a surface of the compressible pad thereof, and in which said projections fit into their mating holes.

14. A stabilizer according to claim 1, in which each organ wall-contacting element comprises a rigid part having a plurality of holes and a pad assembly removably affixed thereto, the pad assembly comprising a flexible pad and a rigid pad-supporting member, the rigid pad-supporting member of the pad assembly of each organ wall-contacting element having plural projections, each said projection mating with one of the plurality of holes in its rigid part, in which the organ wall-contacting surface of each said element is a surface of the compressible pad thereof, and in which each projection has a compressible enlargement which, when relaxed, is larger than the hole with which it mates, and wherein said projections fit into their mating holes with a snap fit.

15. A stabilizer according to claim 1, including a fluid conduit, and in which at least one of the organ wall-contacting members includes a plurality of ports connected to the fluid conduit.

16. A stabilizer according to claim 1, including a light-conducting conduit and means, attached to one of the organ wall-contacting elements and connected to receive light through the conduit, for receiving light from the light-conducting conduit, and emitting said light to provide illumination at a surgical site adjacent to said wall-contacting elements.

* * * * *